(12) United States Patent
Wiechers et al.

(10) Patent No.: US 9,400,265 B2
(45) Date of Patent: Jul. 26, 2016

(54) SWITCHING VALVE FOR HIGH-PERFORMANCE LIQUID CHROMATOGRAPHY

(71) Applicants: Joachim Wiechers, Planegg (DE); Hermann Hochgraeber, Offenberg-Neuhausen (DE)

(72) Inventors: Joachim Wiechers, Planegg (DE); Hermann Hochgraeber, Offenberg-Neuhausen (DE)

(73) Assignee: DIONEX SOFTRON GMBH, Germering (DE)

( * ) Notice: Subject to any disclaimer, the term of this patent is extended or adjusted under 35 U.S.C. 154(b) by 78 days.

(21) Appl. No.: 13/961,637

(22) Filed: Aug. 7, 2013

(65) Prior Publication Data

US 2014/0042351 A1    Feb. 13, 2014

(30) Foreign Application Priority Data

Aug. 10, 2012   (DE) .......................... 10 2012 107 380

(51) Int. Cl.

| F16K 25/00 | (2006.01) |
| G01N 30/26 | (2006.01) |
| G01N 30/22 | (2006.01) |
| F16K 3/10 | (2006.01) |
| F16K 11/074 | (2006.01) |
| G01N 30/20 | (2006.01) |

(52) U.S. Cl.
CPC *G01N 30/26* (2013.01); *F16K 3/10* (2013.01); *F16K 11/0743* (2013.01); *G01N 30/22* (2013.01); *G01N 2030/202* (2013.01)

(58) Field of Classification Search
CPC ....... F16K 11/0743; F16K 3/10; G01N 30/26; G01N 30/22; G01N 2030/202
USPC ......... 251/205, 191, 192, 157, 304, 208, 209, 251/181, 176, 180; 137/625.17, 625.46
See application file for complete search history.

(56) References Cited

U.S. PATENT DOCUMENTS

| 3,203,249 A | * | 8/1965 | Jentzsch | ................ G01N 30/20 137/625.21 |
| 3,237,739 A | * | 3/1966 | Pritchard | .................... 192/99 A |
| 3,297,053 A | * | 1/1967 | McKinney | ................ 137/625.46 |
| 3,384,118 A | * | 5/1968 | Heintz et al. | ............. 137/625.21 |

(Continued)

FOREIGN PATENT DOCUMENTS

| DE | 438244 | 12/1926 |
| DE | 2934346 A1 | 11/1980 |

(Continued)

OTHER PUBLICATIONS

U.S. Appl. No. 13/979,407, filed Jul. 12, 2013.

*Primary Examiner* — Marina Tietjen
*Assistant Examiner* — Umashankar Venkatesan
(74) *Attorney, Agent, or Firm* — Timothy J. Ohara (57) ABSTRACT

A switching valve is described that has a stator which is arranged in a housing and which has multiple connection ports. The switching valve also has a rotatable rotor which is arranged in the housing and which, in predetermined switching positions defined by associated angular positions, interacts with the stator for the fluidic connection or separation of predetermined connection ports. The rotor is rotatably mounted, and acted on with a predefined pressing force in the direction of the stator, by means of a bearing and pressing device arranged in the housing. The bearing and pressing device has a spring device which exerts a load on the rotor or on an element that is capable of performing a wobbling movement.

21 Claims, 3 Drawing Sheets

(56) References Cited

U.S. PATENT DOCUMENTS

| | | | |
|---|---|---|---|
| 3,405,539 | A | 10/1968 | Tanaka |
| 3,417,768 | A * | 12/1968 | Wasson ............................ 137/73 |
| 3,542,071 | A * | 11/1970 | Debbrecht et al. ........ 137/625.46 |
| 4,156,437 | A * | 5/1979 | Chivens et al. ................ 137/554 |
| 4,444,066 | A * | 4/1984 | Ogle et al. .................. 73/863.72 |
| 4,501,297 | A | 2/1985 | Baker |
| 4,722,507 | A * | 2/1988 | Lindackers et al. ............. 251/80 |
| 6,491,063 | B1 | 12/2002 | Benatav |
| 2010/0276617 | A1 * | 11/2010 | Yasunaga ................. 251/129.11 |
| 2010/0281959 | A1 | 11/2010 | Berndt |
| 2011/0006237 | A1 * | 1/2011 | Tower ........................... 251/304 |
| 2012/0061604 | A1 | 3/2012 | Nowak |
| 2013/0284959 | A1 * | 10/2013 | Hochgraeber et al. ... 251/129.11 |

FOREIGN PATENT DOCUMENTS

| | | |
|---|---|---|
| DE | 102011000104 B4 | 2/2013 |
| EP | 0356420 A2 | 8/1989 |
| EP | 1304516 A2 | 4/2003 |
| EP | 2381124 A1 | 10/2011 |
| GB | 2043207 A | 4/1983 |
| WO | 9616277 A1 | 5/1996 |
| WO | 2009101695 A1 | 8/2009 |
| WO | 2011008657 A2 | 1/2011 |
| WO | 2012095097 A1 | 7/2012 |

* cited by examiner

SWITCHING VALVE FOR HIGH-PERFORMANCE LIQUID CHROMATOGRAPHY

CROSS-REFERENCE TO RELATED APPLICATION

This application is claims the priority benefit under 35 U.S.C. §119 to German Patent Application No. 10 2012 107 380.5, filed on Aug. 10, 2012, the disclosure of which is incorporated herein by reference.

FIELD OF THE INVENTION

The invention relates to a switching valve, in particular a high-pressure switching valve for high-performance liquid chromatography (HPLC).

BACKGROUND

In HPLC, high-pressure switching valves are used for a wide variety of different tasks, for example for extracting a sample to be examined from a sample vessel, feeding said sample into a sample loop and introducing the sample from there into a high-pressure liquid stream in the direction of a chromatography column, or for flushing various components or for switching between multiple columns.

Such switching valves are generally installed in automatic sample input devices for HPLC, in column ovens or in fraction collectors.

When using switching valves, it is almost always advantageous for the medium to be controlled to flow through only short capillary paths between the respective components. For example, in the case of samples being conducted in an eluent flow, it is advantageous for only short capillary paths to have to be covered, because then the dispersion of the sample, that is to say the mixing of the sample with the eluent situated in the fluid path upstream and downstream of the sample, is low. Furthermore, as a result of the short capillary paths, the pressure loss in the respective system is minimized.

To attain short capillary paths, it is advantageous, or in many cases imperative, for the switching valve to be of the most compact construction possible. In this way, the switching valve can be used in a space-saving and variable manner.

Despite a compact construction, a switching valve of said type must self-evidently also ensure precise and reproducible positioning of the moving parts which guide the medium to be controlled.

Switching valves such as are used for introducing a sample into the fluid stream normally have a stator in which there are provided multiple connection ports for the supply and discharge of the fluid to and from the switching valve. The ports are connected via ducts to opening cross sections which are formed on a switching surface of the stator, for example on the face side of a substantially cylindrical stator element. The rotor likewise has a switching surface which interacts with the switching surface of the stator, wherein in the switching surface of the rotor there are formed grooves which serve to connect certain opening cross sections and/or ports of the stator to one another as a function of two or more switching positions. Here, the rotor and the stator must be pressed against one another with an adequately high pressing force in order to attain a sealing action in the plane of the switching surfaces even in the case of high pressures such as arise in liquid chromatography, in particular HPLC.

Such switching valves are described for example in WO 2009/101695 A1 or in US 2010/0281959 A1.

SUMMARY

In recent times, in HPLC, owing to the high pressures used here for the medium to be controlled, the stator and the rotor have been designed such that the two interacting surfaces are composed in each case of a hard material or are coated with a hard material. In this case, it is necessary for the rotor to be mounted such that it can perform a wobbling movement through sufficient angles with respect to the stator in order to compensate manufacturing and assembly tolerances and generate the most uniform pressure distribution possible in the contact surface in all angular positions. For this purpose, it is known for the rotor to be mounted, such that it can perform a wobbling movement, by means of a flexible cushion (for example DE 10 2011 000 104, not previously published; similar to WO 2011/008657 A2). It is the intention to be able to also realize such functionality in the case of the valve according to the present invention.

The invention is therefore based, taking the prior art mentioned in the introduction as a starting point, on the object of providing a switching valve, in particular a high-pressure switching valve for high-performance liquid chromatography, which switching valve exhibits, in each rotary position of the rotor, as homogenous as possible a pressure distribution in the contact surface between the rotor and the stator in a manner as independent as possible of manufacturing and assembly tolerances, in which switching valve precise guidance and positioning of the rotor is simultaneously ensured, and which switching valve has a simple compact construction.

The invention is based on the realization that it is possible for the spring device, which is required in any case for generating the pressing force between the rotor and stator, to be designed such that, at the same time, a compensation or wobbling movement of the rotor required owing to assembly tolerances or production tolerances is permitted and nevertheless a substantially uniform pressure distribution is ensured in the contact surface between the rotor and stator. This yields an extremely compact and also simple construction.

In one embodiment of the invention, the spring unit may be supported on a rotatably mounted receiving element of the bearing and pressing device, on which receiving element there is provided a drive region for coupling to a rotary drive, preferably in the form of an electromotive drive. In this way, rotatable mounting of the spring unit is attained in a simple manner. As a result of the connection of a drive to the receiving element rather than to the spring unit, axial decoupling is attained because a drive region provided on the receiving element is positionally fixed in the axial direction of the valve and of the rotor (more precisely: in the direction of the axis of rotation of the rotor).

Here, the spring unit may be fixedly connected to or formed in one piece with the rotatably mounted receiving element. This yields a reduction in the number of valve parts to be assembled.

In one preferred embodiment of the invention, the spring unit has one or more plate spring elements. Such spring units are of small construction in the axial direction and may furthermore be dimensioned in a simple manner such that asymmetric spring deflections, in particular spring deflections in the plane of the spring unit in which the spring unit exerts load directly on the rotor or on an element connected thereto, lead to substantially no change or to only a very small change in the pressure distribution in the contact surface between the rotor and the stator. In other words: the restoring moment of the spring unit into the initial position, in which the load exertion plane between spring unit and the rotor or the element connected thereto is perpendicular to the axis of the spring unit, can be selected to be very low or even zero. Said restoring moment will also be referred to hereinafter as directional moment.

In one embodiment of the invention, the one or more plate spring elements is/are of annular, preferably circular-ring-shaped form. For the configuration of the desired characteristic, the plate spring elements may also be provided with outwardly and/or inwardly open radial slots.

For the radial positioning of the rotor in relation to the stator, the plate spring element or one of the multiple plate spring elements may act on the rotor, or on the element which is directly or indirectly connected to said rotor, by means of a positive fit which accommodates radial forces. For example, the rotor may have, on its side facing toward the spring unit, an annular or cylindrical projection which engages with an accurate fit into the central aperture of the facing plate spring element.

Furthermore, for the radial positioning of the rotor in relation to the stator (more precisely: for the positioning of the one or more plate spring elements in relation to the receiving element), the plate spring element or one of the multiple plate spring elements may act on the receiving element by means of a form fit which accommodates radial forces.

In one embodiment of the invention, a single circular-ring-shaped plate spring element or a stack of circular-ring-shaped plate spring elements may be provided, wherein the one or more plate spring elements is/are formed such that the cross-sectional profiles of the circular ring in axial longitudinal section are preferably of substantially rectangular form, wherein the outer and inner face sides of the cross-sectional profiles are formed by circular arcs of a perimeter whose central point lies at the center of area of the respective cross-sectional profile. Here, on the rotor, there is provided at least one projection which has a wall extending parallel to the axis of rotation and substantially parallel to the axis of the plate spring element, which wall is acted on by the inner or outer face side of the plate spring. Additionally, on the receiving element, there is provided at least one projection which has a wall extending substantially parallel to the axis of rotation and substantially parallel to the axis of the plate spring element, said wall being acted on by the in each case other face side of the plate spring. By means of said configuration of the geometry of the plate spring and of the form fits, the compression movement of the plate spring (as viewed in cross section, the tilting movement of the for example approximately rectangular cross-sectional profiles about the center of area) is hindered practically only by the frictional resistance on the contact surfaces. The spring characteristic is not changed or impaired, or is at most changed or impaired only insignificantly, by the form fit.

In a further embodiment of the invention, the at least one plate spring element has an annular, in particular circular-ring-shaped plate spring region which, at its outer edge, is connected via at least one wall to a substantially rigid annular support part and, at its inner edge, is connected via at least one wall to a base part, wherein, in the assembled state of the switching valve, the base part transmits the pressing force to the rotor or to the element which is directly or indirectly connected to said rotor. Here, the entire plate spring element is preferably formed in one piece and preferably has a double pot-shaped structure. The walls, of which there are at least one, preferably extend in each case in a direction pointing away from the support part or from the plate spring region and from the stator. Here, the walls (in the unloaded state of the plate spring element) need not imperatively run axially parallel. This is however advantageous because, in this case, the walls are loaded substantially only by stresses (in the substantially axially parallel direction). However, the compression movement of the plate spring region also results in a movement of the outer edge of the plate spring region radially outward and a movement of the inner edge of the plate spring region radially inward, and thus a corresponding (additional) exertion of bending load on the walls, of which there are at least one. Here, the walls are designed and dimensioned such that deformations of the walls resulting from the compression movement of the plate spring region take place within the elastic range of the walls.

Here, the walls, of which there are at least one, may be designed and dimensioned in such a way that the walls have a rigidity under extension in the longitudinal direction of extent such that the spring travel of the plate spring element is defined substantially exclusively by the spring travel of the plate spring region, and that the walls have a rigidity under bending such that radial movements of the outer and inner edges of the plate spring regions, and tilting movements of the cross-sectional profiles of the plate spring region in axial longitudinal section, generated by compression movements of the plate spring region are permitted by bending deformation of the walls.

The walls, of which there are at least one, may advantageously be designed and dimensioned such that restoring forces and/or restoring moments generated by the walls during said bending deformations are so low that the spring characteristic of the plate spring region, such as is provided in the case of an unhindered compression movement, remains substantially unchanged.

The walls may be in each case of encircling form and are dimensioned and configured such that the plate spring region and the base part are held rigidly with respect to translatory movements in the plane perpendicular to the axis of the plate spring region such that secure radial positioning of the rotor relative to the stator is ensured.

In another embodiment, in each case such a number of walls may be provided in a manner distributed over the circumference, and the individual walls may be dimensioned and configured in such a way, that the plate spring region and the base part are held rigidly with respect to translatory movements in the plane perpendicular to the axis of the plate spring region such that secure radial positioning of the rotor relative to the stator is ensured.

In said embodiments, the base part may have one or more coupling elements for the radial positioning of the rotor and for the rotationally conjoint connection to the rotor. Said coupling elements may be pins which run in an axially parallel manner and which are anchored in the base part and engage into corresponding recesses in the stator.

BRIEF DESCRIPTION OF THE DRAWINGS

The invention will be explained in more detail below on the basis of embodiments illustrated in the drawing, in which.

DETAILED DESCRIPTION OF EMBODIMENTS

Figure 1:
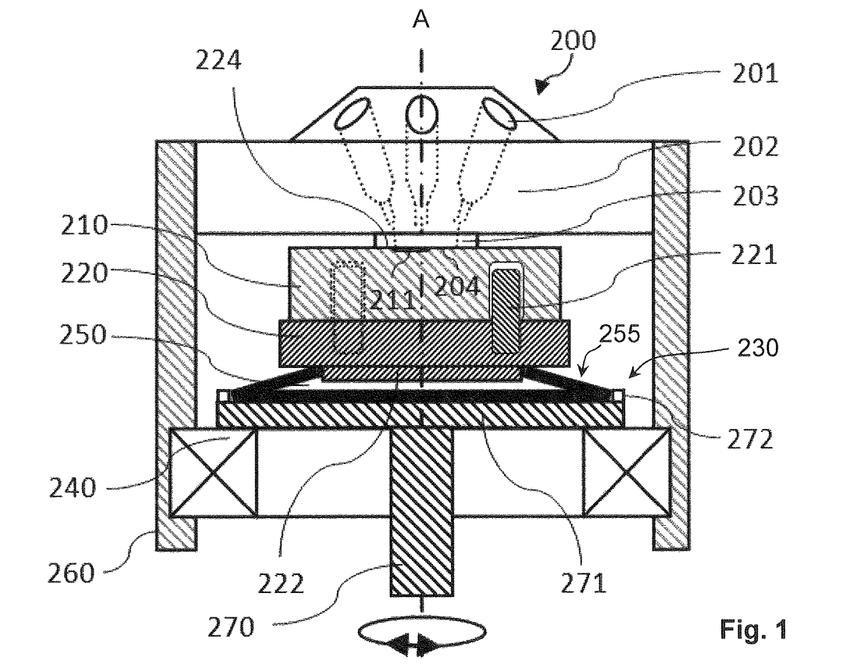
FIG. 1 shows an axial longitudinal section through a schematically illustrated first embodiment of a switching valve according to the invention.

The first embodiment of a switching valve 200 illustrated in FIG. 1, said switching valve also being suitable for HPLC, is composed of a housing 260 in which a stator 202 is held in a positionally fixed manner. The stator 202 has recesses 201 which run in a radially inwardly oriented manner and which continue in port ducts which run in an axial direction into a protruding, substantially circular projection 203. In the circular stator face surface 224 of the projection 203, the port ducts open out in corresponding cross-sectional openings. The stator face surface 224 interacts with a rotor face surface 204 of a rotor 210 which, in the housing 260 of the switching valve 200, is rotatably mounted, and acted on with a predefined pressing force in the direction of the stator 202, by means of a bearing and pressing device 230. The bearing and pressing device 230 also performs the centering of the rotor 210 relative to the stator 202, such that the axis of rotation of the rotor 210 is as far as possible aligned with the axis A of the stator 202. It is achieved in this way that grooves 211, which run predominantly coaxially and in the circumferential direction of a coaxial circle, in the rotor face surface 204 are positioned exactly in relation to the cross-sectional openings, provided in the stator face surface 224, of the port ducts. In certain rotational positions of the rotor 210, it is possible in this way for respectively predetermined cross-sectional openings of the port ducts to be fluidically connected to one another or separated from one another.

It is pointed out at this juncture that port connectors may be inserted into, preferably screwed into, the recesses 201, by way of which port connectors lines in the form of capillaries for the supply and discharge of a liquid medium can be connected to the stator 202 or to the switching valve 200.

Figure 2:
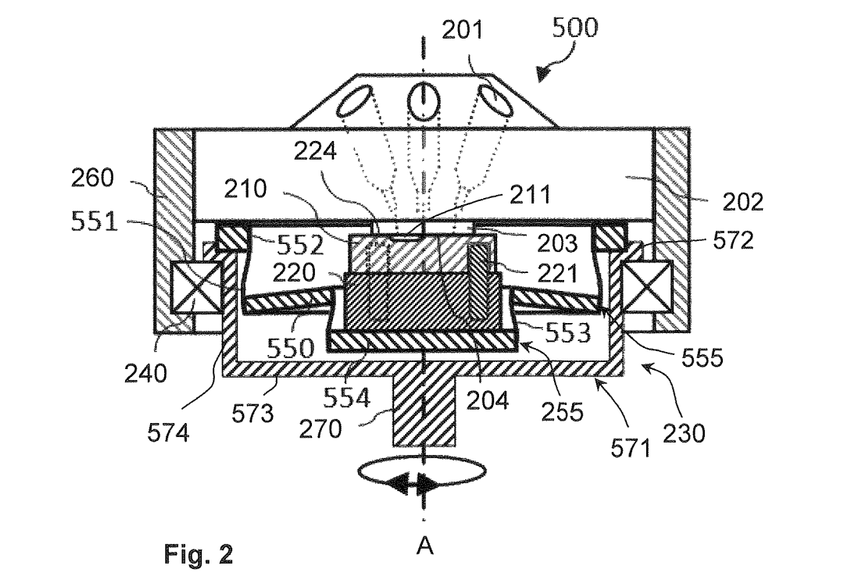
FIG. 2 shows an axial longitudinal section through a schematically illustrated second embodiment of a switching valve according to the invention.

At the extremely high pressures prevailing in HPLC, the rotor 210 must be pressed by way of the rotor face surface 204 against the stator face surface 224 with an adequately high pressing force in order to ensure a sealing action in the contact surface between the rotor 210 and stator 202. To prevent damage to the face surfaces 204 and 224 which are normally composed of hard (for example ceramic) materials, it is necessary to attain as uniform as possible a pressure distribution in the sealing surface. A uniform pressure distribution furthermore ensures that the face surfaces 204 and 224 which move relative to one another are subjected to the least possible wear. Here, the contact surface (sealing surface) between the rotor 210 and stator 202 may be of planar design, as shown in FIGS. 1 and 2. The sealing surface may however also have any other desired profile, for example a conical or spherical profile.

In order to attain as uniform a pressure distribution as possible in the sealing surface in all rotational positions of the rotor 210, it has proven to be advantageous to dispense with a rigid rotor axle because, in this case, even the slightest assembly tolerances or production tolerances would lead to a non-uniform pressure distribution in the sealing plane (formed by the stator face surface 224 and rotor face surface 204), and in the extreme case, leaks would occur in the sealing plane, or damage to the rotor face surface or stator face surface would occur.

For this purpose, the bearing and pressing device 230 has a coupling element 220 which is connected to the rotor 210 and which is acted on with a predetermined pressing force in the direction of the stator 202 by means of a spring unit 255 in the form of a plate spring 250. The pressing force should self-evidently be selected to be so high that the contact pressure generated in the sealing surface is sufficient to ensure the sealing action of the switching valve 200.

The connection between the coupling element 220 and the rotor 210 is realized by means of a plurality of, for example three, pins 221 which run axially parallel with respect to the rotor axis and which engage into corresponding recesses in the rotor 210. In this way, a rotationally conjoint but releasable connection between the rotor 210 and the coupling element 220 is ensured. The pins 221 may be provided along a coaxial circle in the coupling element 221 so as to be distributed over the circumference of said coupling element.

The plate spring 250 is supported against a receiving element 271 of the bearing and pressing device 230, which receiving element is mounted in the housing 260 so as to be rotatable by means of a bearing 240 and so as to be fixed in an axial direction. The receiving element 271 may, for fixing in the radial direction, have a shoulder (not illustrated) which engages into the inner ring of the bearing 240. Furthermore, the rotatable bearing part may also be formed in one piece with the receiving element 271. The receiving element 271 has a drive region 270 which is provided axially in the exemplary embodiment illustrated and which is in the form of a shaft provided coaxially. Said drive region 270 may be coupled to a drive (not illustrated), for example an electromotive drive. Owing to the axially fixed mounting of the receiving element 271 and thus also of the drive region 270, simple coupling between the drive region 270 and the drive is made possible.

The receiving element 271 has projections 272 which protrude in the direction of the stator and which are positioned such that the outer circumference of the spring unit 255 in the form of a plate spring 250 can be supported against the projections 272. In this way, centering of the spring unit 255 relative to the axis of rotation A of the bearing and pressing device 230 or of the receiving element 271 is attained.

Instead of multiple projections along the outer circumference of the spring unit 255, it is self-evidently also possible for one encircling projection 272 to be provided.

By way of its other end, the spring unit 255 or the plate spring 250 exerts load on the underside of the coupling element 220. The geometry of the switching valve and the structure or the geometry of the spring unit 255 are selected here such that, in the assembled state of the switching valve 200, a spring travel is realized which is sufficient to generate the necessary pressing force between the rotor 210 and stator 202.

For the centering of the coupling element 220 and thus also of the rotor 210 in relation to the stator 202, the coupling element 220 has, on its underside facing toward the spring unit 255, a projection 222, the cross section or outer circumference of which is selected so as to engage with an accurate fit into a recess in that side of the spring unit 255 which faces toward the coupling element 220. In the exemplary embodiment illustrated in FIG. 1, the recess is formed by the circular recess of the plate spring 230. Centering of the spring unit 255 relative to the receiving element 271 is thus attained, and at the same time, the spring unit 255 generates centering of the coupling element 220 and thus of the rotor 210 in relation to the stator 202. In addition to the generation of the pressing force, the bearing and pressing device, in particular the spring unit 255, thus also performs the centering function.

At the same time, the characteristic of the spring unit 255 may be configured such that a wobbling movement of the coupling element 220 and thus also of the rotor 210 is made possible. Such wobbling movements must be ensured if the face surface 224 of the stator 202 and/or the face surface 204 of the rotor 210 are/is not exactly perpendicular to the axis of rotation of the receiving element 271. The spring unit 255 or the plate spring 250 may be dimensioned such that, at the operating point of the spring unit 255 defined by the spring travel to be effected during the assembly of the switching valve 200 in order to generate the necessary pressing force, small asymmetric deflections of the spring unit 255 (that is to say tilting movements of the stator in relation to the axis of rotation of the receiving element 271) lead only to a small or negligibly small restoring moment (also referred to hereinafter as directional moment). In this way, it can be ensured that, even in the event of tilting of the rotor, the pressure distribution in the sealing surface remains substantially unchanged. A disruption of the valve function as a result of leaks, increased wear or even damage to the surfaces of the mutually opposite rotor face surface 204 and stator face surface 224 is avoided in this way.

It is pointed out that it is self-evidently also possible, instead of the rotor 210 being acted on indirectly via the coupling element 220 with the pressing force generated by the spring unit 255, for the stator 202 to be acted on directly and, for this purpose, for a projection corresponding to the projection 222 to be provided on the underside of the rotor 210 for the purpose of centering the rotor 210.

Instead of a single bearing 240, which may preferably be in the form of an angular-contact ball bearing, for ensuring an axially fixed mounting of the components, it is also possible for a radial bearing and an additional axial bearing to be provided.

The spring unit 255 may be of any desired form as long as the above-described spring characteristic with an adequately low directional moment is ensured.

Instead of a single plate spring 250, it is self-evidently also possible for a stack of multiple plate springs to be used.

Figure 3A:
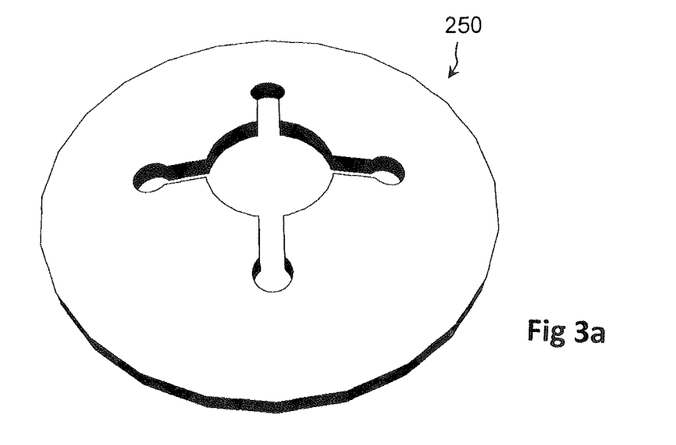
FIG. 3a shows a variant of a spring unit for an embodiment of a switching valve as per FIG. 1 in the form of a plate spring with radial slots, which run in a radially inner region, for setting a desired spring characteristic.
Figure 3B:
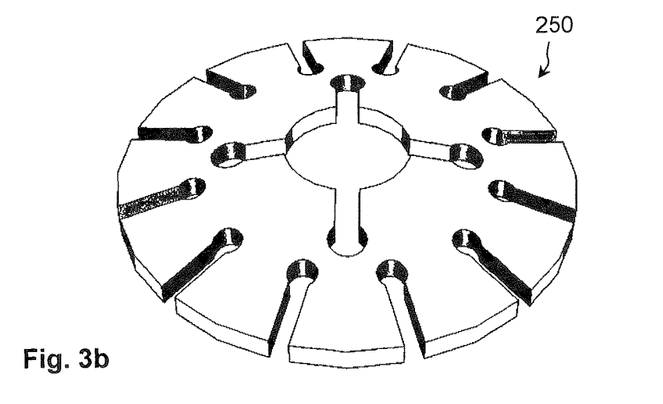
FIG. 3b shows a variant of a spring unit for an embodiment of a switching valve as per FIG. 1 in the form of a plate spring with radial slots, which run in a radially inner region and additionally in a radially outer region, for setting a desired spring characteristic.

The plate spring 250 or the stack of plate springs may be formed from variants of plate springs illustrated in FIGS. 3a and 3b. These are plate springs which are curved in the usual way and which have a predetermined thickness, wherein, to generate the desired spring characteristic, the radially inner region of the plate spring 250 and/or the radially outer region of the plate spring 250 may be provided with multiple radially running slots which extend in each case from the inner edge of the plate spring 250 into the radially inner region or from the outer edge of the plate spring 250 into the radially outer region.

A problem of the embodiment as per FIG. 1 is that the plate spring 250, in the case of a reduction of the curvature of the plate spring, is impaired in terms of its spring characteristic by the projections 272 and by the projection 222 to be centered. This will be explained in more detail below on the basis of FIG. 6. In the case of a compression movement of the plate spring 250, the inner diameter of the plate spring and also the outer diameter fundamentally change. This is because, during a compression movement, a tilting movement of the cross-sectional profiles (see FIG. 6), which are approximately rectangular in longitudinal cross section of the plate spring 250, takes place about the respective center of area S.

Figure 6:
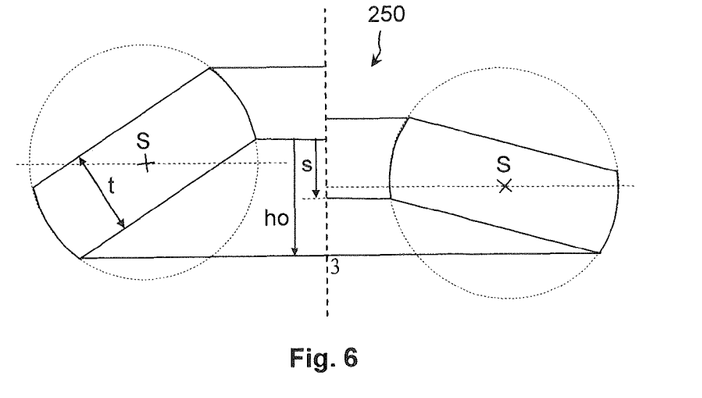
FIG. 6 is a schematic illustration of a plate spring in axial longitudinal section.

If, during a spring deflection, that is to say during a compression movement, the plate spring 250 is hindered in terms of said movement or said radial movement is even blocked, this leads to a drastic change in the spring characteristic.

One variant for eliminating or lessening said problem is the configuration of the plate spring as per FIG. 6, such that the cross-sectional profiles in the axial longitudinal section are delimited at the inner and outer edges by circular lines which lie on a circle whose central point coincides with the center of area of the cross-sectional profiles.

In this case, too, as can be seen from FIG. 6, a change in the outer or inner diameter of the plate spring 250 occurs if the geometry of the initial position for a compression movement (for example the left-hand position in FIG. 6) is configured such that the circular line, which delimits the outer and inner edges, of the respective cross-sectional profile does not intersect the horizontal line through the center of area S about which the tilting movement or compression movement takes place. If the spring is moved from the position illustrated at the left in FIG. 6 into the position illustrated at the right in FIG. 6, that is to say if the spring 250 is deflected by the spring travel s, the top edge of the outer end, that is to say the left-hand upper corner of the left-hand cross-sectional profile, moves above the radially outermost point of the circle (point of intersection of the circle with the horizontal line through the center of mass S). The outer diameter of the plate spring 250 thus changes. The same applies to the right-hand lower corner of the left-hand cross-sectional profile, such that the inner diameter of the plate spring 250 also changes.

If, proceeding from the position of the plate spring 250 illustrated at the right in FIG. 6, a further slight spring deflection, that is to say an increase of the spring travel s, were effected, then neither the inner diameter nor the outer diameter of the plate spring would change, because it is merely the case that a pivoting movement of the cross-sectional profiles takes place which is such that the horizontal line through the center of mass S continues to intersect the outer or inner circular line delimiting the cross-sectional profile. In other words, the inner diameter and outer diameter of the plate spring remain constant in the event of such a deflection movement or compression movement of the plate spring 250.

If the abutment surfaces at the inner edge and at the outer edge are of complementary design, for example, in the case of the embodiment as per FIG. 1, the abutment surfaces on the projection 222 of the coupling element 220 and the abutment surfaces on the projection 272 of the receiving element 271, the result is a plain bearing with a correspondingly large contact surface. The axially parallel circumferential surfaces of the projection 222 and of the projection 272 illustrated in FIG. 1 are however self-evidently also sufficient for ensuring the centering action.

In this case, the plate spring 250 may be dimensioned such that, during the assembly process, the plate spring 250, in the initial state, still has an inner diameter considerably larger than the outer diameter of the projection 222 and has an outer diameter smaller than the inner diameter of the projection 272. If, during the assembly process, the plate spring 250 is compressed or deflected as far as the operating point in order to generate the required pressing force between the rotor 210 and stator 202, then at said operating point the plate spring 250 should correspond, at its inner diameter, to the outer diameter of the projection 222 and, at its outer diameter, to the inner diameter of the projection 272 in order to ensure the desired centering action. At said operating point, a state should then also be attained in which, as illustrated on the right in FIG. 6, the horizontal line through the center of mass S of the cross-sectional profiles of the plate spring 250 intersects the circular lines of the inner edge and of the outer edge of the cross-sectional profiles. With suitable dimensioning, further slight deflection movements or tilting movements of the coupling unit 220 or of the rotor 210 then no longer lead to a change in the outer or inner diameter of the plate spring 250, such that the spring characteristic thereof is not impaired as a result.

In conclusion with regard to said problem, it is pointed out that it is possible for the inner diameter and the outer diameter of a plate spring to be held constant even if the cross-sectional profiles of the plate spring in axial longitudinal section do not run parallel to one another but rather, for example, have a slight (plate-shaped) curvature. The solution explained above is possible whenever the face sides of the cross-sectional profiles are delimited by circular lines of a circle whose central point coincides with the center of mass of the cross-sectional profile. Furthermore, the geometry must be configured such that, at the operating point of the plate spring, the horizontal line through the circle central point intersects the circular lines, which delimit the face sides of the cross-sectional profiles, in all possible positions of the plate spring (within the entire spring travel of interest proceeding from the operating point).

The plate spring 250 in FIG. 1 may conversely also be provided such that the spring opening faces toward the receiving element 271. It is self-evidently necessary in this case for the projections 222 and 272 to also be interchanged, that is to say a projection similar to the projection 272 must be formed on the rotor underside or on the underside of the coupling element 220, and a projection similar to the projection 222 must be formed on the receiving element 271.

The second embodiment of a switching valve 500 according to the invention illustrated in FIG. 2 has substantially the same components as the embodiment as per FIG. 1. Therefore, identical or functionally identical elements or devices are denoted by identical reference signs. With regard to the design and mode of operation thereof, reference may therefore be made to the statements made above.

The embodiment as per FIG. 2 differs from the embodiment as per FIG. 1 substantially in that the receiving element 571 has a substantially pot-shaped structure. An upper flange region 572 of the receiving element 571 is supported on the bearing 240. The bearing 240 again serves for the mounting of the receiving element 571 such that the latter is rotatable about the axis of rotation A, wherein the mounting is provided such that the receiving element 571 can, in the axial direction, accommodate the entire pressing force between the rotor 210 and stator 202.

On the underside of the base 573 of the pot-shaped receiving element 571 there is, in turn, provided a drive region 270 in the form of a coaxially formed shaft. The drive region is preferably formed in one piece with the base 573.

The encircling wall 574 of the receiving element 571 has an outer diameter which corresponds to the inner diameter of the bearing 240, such that radial centering of the receiving element 571 is realized in this way.

On the flange region 572 of the receiving element 571 there is supported a plate spring element 555 which has substantially a double pot-shaped structure in axial longitudinal section. The plate spring element 555 has a substantially rigid annular support part 552 which is supported on the flange region 572 of the receiving element 571. The flange region 572 may, for this purpose, have a shoulder on its top side facing toward the stator, on which shoulder the support part 552 is supported, wherein the geometry of the support part 552 is selected such that it interacts with a suitably selected, preferably complementary geometry of the shoulder of the flange region 572, such that the support part 552 is centered and held fixed in the radial direction.

The support part 552 is connected by way of an encircling wall 551, which extends in a substantially axial direction, to a plate spring region 550 of the plate spring element 555. Aside from its connection to the encircling wall 551 at its outer edge and the connection to a further, substantially axially extending encircling wall 553, the plate spring region may be formed at its inner edge in the same way as a separate plate spring 250 as explained above.

The further encircling wall 553 is connected, at its lower end facing away from the stator, to a base part 554 which may be of substantially planar form.

Since the encircling walls 551 and 553 extend in each case away from the stator in the axial direction, said walls are loaded substantially under tension by the pressing force to be transmitted from the plate spring region 550 to the stator 202.

It is self-evidently also possible, instead of in each case one encircling wall 551, 533, for a number of walls distributed over the circumference to be provided. Here, each of the individual walls may extend over a particular circumferential region. The encircling wall 551, 553 or the multiple individual walls are in each case designed and provided so as to generate an adequate centering action for the plate spring region 550 and the base part 554 in the radial direction (or in a plane perpendicular to the axis of rotation A). In other words, the walls are designed and provided such that a translatory movement of the base part 554 and/or of the plate spring region 550 (that is to say a displacement movement in a plane substantially perpendicular to the axis of rotation A) is blocked, or the plate spring element 555 has, in said plane, a stiffness high enough to ensure the centering action.

By contrast, the walls 551 and 553 are preferably designed and dimensioned such that radial movements of the outer and inner edges of the plate spring region 550 are permitted by corresponding bending of the walls 551, 553, without the radial restoring forces generated by the walls causing a significant change in the spring characteristic of the plate spring region 550. Also, no friction forces, which would lead to hysteresis behavior of the spring element, can arise between the plate spring region 550 and adjacent elements.

Said embodiment has the advantage that, in the configuration of the plate spring region 550, it is no longer necessary to ensure that the inner diameter and/or the outer diameter remain constant during compression movements of the plate spring region 550.

In turn, on the base part 554 of the plate spring element 555, there is (preferably centrally or coaxially) arranged a coupling element 220 which, as is also the case in the embodiment as per FIG. 1, bears the rotor 210 such that the latter is centered relative to the stator 202 in the plane perpendicular to the axis of rotation A. The rotor 210 in turn is connected rotationally conjointly but releasably to the coupling element 220 by means of pins 221.

The connection of the coupling element 220 to the base part 554 may be releasable or fixed. Also, the coupling element 220 may be formed in one piece with the base part 554. In any case, the coupling element 220 must be dimensioned such that a bending movement of the wall 553 is not blocked.

It is also possible for the coupling element 220 illustrated in FIG. 2 to be dispensed with entirely if means are provided in the base part 554 for receiving the rotor 210 in a rotationally conjoint manner.

Figure 4:
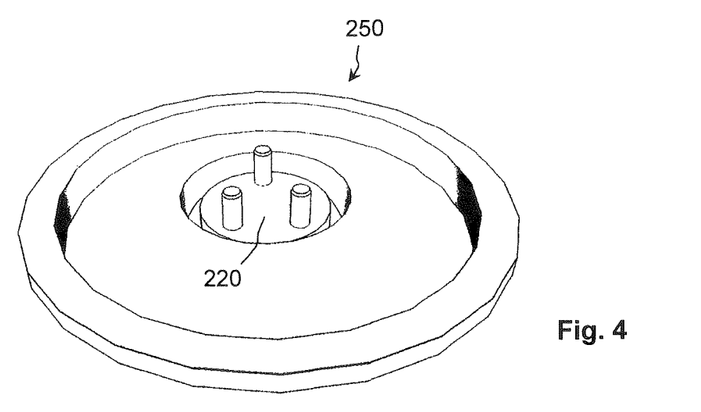
FIG. 4 shows a variant of a spring unit for an embodiment of a switching valve as per FIG. 2 with a plate spring region which is connected in each case via an encircling wall, which runs in an essentially axially parallel manner, to an outer support part and to an inner base part.

As a result of the design of the plate spring element 555, which is illustrated once again in FIG. 4 in a perspective view, an extremely compact structural form of the switching valve 500 in the axial direction is made possible. The walls 551, 553 function as solid joints and permit the deflection of the plate spring even if the relevant compression movement of the plate spring may lead to a change in the outer diameter and/or inner diameter (in a projection onto a plane perpendicular to the axis of rotation A) (see explanation with regard to FIG. 6). This also applies in the case of an asymmetrical loading of the plate spring region 550 if wobbling movements of the rotor 210 occur. Both the embodiment as per FIG. 1 and also the embodiment as per FIG. 2 show a switching valve 200, 500 which is composed of a very small number of individual components and which can therefore be assembled simply and quickly.

Since the components, including the spring unit 255, in particular a plate spring 250 or a plate spring element 555, can be manufactured from temperature-resistant materials such as, for example, steel (in particular high-grade steel), excellent temperature resistance of the switching valve is also realized. A long service life is simultaneously attained.

Finally, advantageous dimensioning of a spring unit according to the invention, in particular of a plate spring 250 or of a plate spring element 555, will be explained briefly on the basis of the diagram illustrated in FIG. 5.

Figure 5:
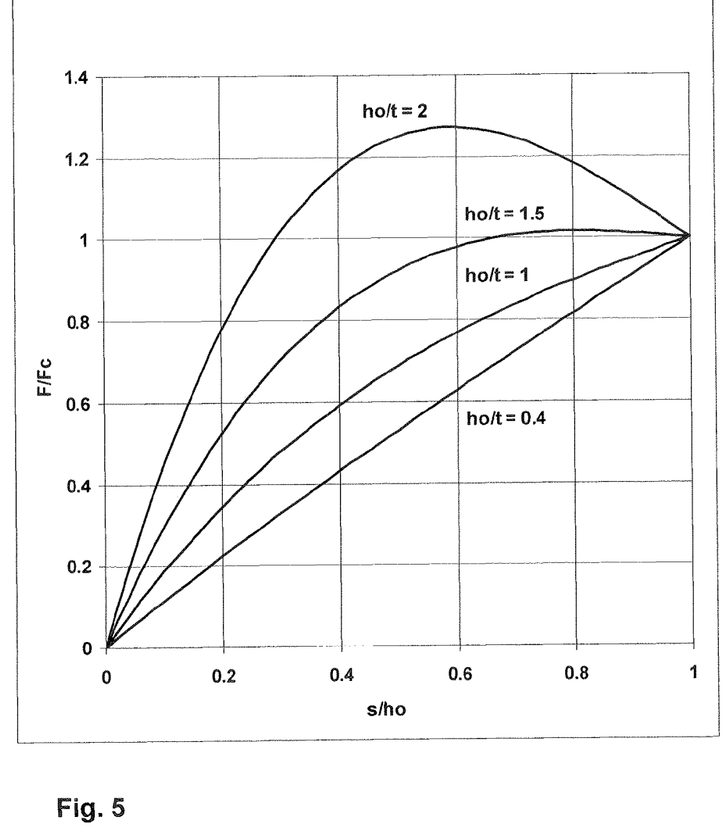
FIG. 5 shows a diagram for explaining the characteristic of a spring unit which is particularly suitable for the purposes of the invention, in particular of a plate spring or of a plate spring region as per FIG. 6.

The horizontal axis of the diagram in FIG. 5 shows the spring travel s, normalized with respect to the maximum spring travel ho, of a plate spring or of a plate spring region in the case of a (symmetrical) compression of the plate spring (compression movement) in the axial direction. The vertical axis shows the spring force F normalized with respect to the spring force $F_C$ attained at the maximum spring travel ho, wherein the spring force F corresponds to the pressing force between the rotor and stator.

The parameter of the individual curves is the maximum spring travel ho in relation to the material thickness or thickness t of the plate spring or of the plate spring region.

As can be seen from FIG. 5, plate springs with a large wall thickness t have an approximately linear profile of the spring characteristic. With decreasing material thickness, the profile becomes ever more non-linear, wherein above a value of approximately $ho/t=\sqrt{2}$, an extreme is even passed through at which the differential spring constant (tangent to the curve profile) is equal to 0.

Since it is advantageous for the switching valve if, during the assembly process, a defined, predetermined pressing force is generated in as precise a manner as possible at the operating point, it is expedient for the spring characteristic to be defined such that as horizontal as possible a profile is generated at the operating point (and in the direct vicinity thereof). It is expedient to use plate springs which are dimensioned such that, at the operating point which is attained in the assembled state of the switching valve and in which the at least one plate spring is preloaded, they have as flat as possible a profile. In this way, it is attained that assembly tolerances lead to only small changes in the pressing force between the rotor 210 and stator 202.

The same also applies to the directional moment of the plate spring at the operating point. It has been found that, with the dimensioning of the plate spring as explained above, the directional moment is also so small, or through suitable configuration of the plate spring can be made so small, that asymmetrical spring movements (that is to say a spring movement generated by a tilting of the underside of the stator) lead to a relatively small directional moment.

It is advantageous in particular for the plate spring or the spring unit to be dimensioned such that, when the maximum spring travel ho is reached, the spring characteristic runs substantially horizontally. If the operating point is selected so as to be situated a short distance before (or if appropriate after) the attainment of the maximum spring travel (and is at a distance therefrom sufficient to permit symmetrical or asymmetrical spring movements for the wobbling movement of the rotor), the result here is a large tolerance with respect to assembly or production tolerances, and simultaneously the desired small directional moment.

Finally, it is pointed out that said basic dimensioning specification applies not only to the above-described specific exemplary embodiments using plate springs or plate spring regions, but rather basically for any type of spring unit which permits a configuration of the spring characteristic in the manner described above.

What is claimed is:

1. A switching valve comprising:
   (a) a stator arranged in a housing, the stator including multiple connection ports;
   (b) a rotor arranged in the housing and having a switching position to form a fluidic connection to predetermined connection ports;
   (c) in which the rotor is rotatably mounted and pressed against the stator with a bearing and pressing device arranged in the housing, the bearing and pressing device comprises a spring unit;
   (d) in which the spring unit supports the rotor, or a coupling element connecting the rotor and the bearing and pressing device and transferring the axial pressure force to the rotor, and exerts an axial pressure force thereon;
   (e) in which the spring unit positions the rotor, or the rotor and the coupling element, radially with respect to the stator; and
   (f) in which only the spring unit supports the rotor, or the rotor and the coupling element, with respect to the stator such that the spring unit enables the rotor, or rotor and coupling element, to wobble when pressed against the stator.

2. The switching valve of claim 1 further comprising the coupling element.

3. The switching valve of claim 1, in which the rotor is coupled to a rotary drive.

4. The switching valve of claim 3, in which the spring unit is supported on a rotatably mounted receiving element of the bearing and pressing device, the receiving element including a drive region coupled to an electromotive rotary drive.

5. The switching valve of claim 4, in which the spring unit is fixedly connected to the receiving element.

6. The switching valve of claim 4, in which the spring unit is formed as one piece with the receiving element.

7. The switching valve of claim 1, in which the spring unit comprises one or more plate spring elements.

8. The switching valve of claim 7, in which the one or more plate spring elements comprises an annular shaped form.

9. The switching valve of claim 8, in which the plate spring element comprises multiple radially running slots extending from an inner edge of the plate spring element into a radially inner region of the plate spring element.

10. The switching valve of claim 8, in which the plate spring element comprises multiple radially running slots extending from an outer edge of the plate spring element into a radially outer region of the plate spring element.

11. The switching valve of claim 7, in which the one or more plate spring elements exerts a load on the rotor to radially position the rotor in relation to the stator, the plate spring element including a form fit to the rotor to accommodate radial forces.

12. The switching valve of claim 4 further comprising: the coupling element, in which the spring unit comprises one or more plate spring elements, and the one or more plate spring elements exerts a load on the coupling element to radially position the rotor in relation to the stator, the plate spring element including a form fit to the coupling element to accommodate radial forces.

13. The switching valve of claim 12, in which the one or more plate spring elements exerts a load on the receiving element to radially position the plate spring element in relation to the receiving element, the receiving element including a form fit to the plate spring element to accommodate radial forces.

14. The switching valve of claim 8, in which
(a) the one or more plate spring element comprises one or more circular-ring-shaped plate spring element,
(b) the circular-ring-shaped plate spring element having a cross-sectional profile in an axial longitudinal section, the cross-sectional profile forming a substantially rectangular form having an outer face side and an inner face side, the outer face side and the inner face side both forming circular arcs as part of a perimeter of a circle having a central point at a center of an area of the cross-sectional profile,
(c) the rotor including at least one projection, the projection of the rotor having a wall extending parallel to an axis of rotation and substantially parallel to an axis of the plate spring element, the wall of the rotor being biased against by the inner face side or the outer face side of the plate spring, and
(d) the receiving element including at least one projection, the projection of the receiving element having a wall extending parallel to an axis of rotation and substantially parallel to an axis of the plate spring element, the wall of the receiving element being biased against by one of the inner face side or the outer face side of the plate spring not being biased against by the wall of the rotor.

15. The switching valve of claim 12, in which
(a) the one or more plate spring element comprises one or more circular-ring-shaped plate spring element,
(b) the circular-ring-shaped plate spring element having a cross-sectional profile in an axial longitudinal section, the cross-sectional profile forming a substantially rectangular form having an outer face side and an inner face side, the outer face side and the inner face side both forming circular arcs as part of a perimeter of a circle having a central point at a center of an area of the cross-sectional profile,
(c) the coupling element including at least one projection, the projection of the coupling element having a wall extending parallel to an axis of rotation and substantially parallel to an axis of the plate spring element, the wall of the coupling element being biased against by the inner face side of the plate spring, and
(d) the receiving element including at least one projection, the projection of the receiving element having a wall extending parallel to an axis of rotation and substantially parallel to an axis of the plate spring element, the wall of the receiving element being biased against the outer face side of the plate.

16. A switching valve comprising:
a stator arranged in a housing, the stator including multiple connection ports;
a rotor arranged in the housing and having a switching position to form a fluidic connection to predetermined connection ports;
in which the rotor is rotatably mounted and pressed against the stator with a bearing and pressing device arranged in the housing;
in which the bearing and pressing device is coupled to the rotor to transmit a pressing force;
in which the rotor is configured to wobble when pressed against the stator;
in which the bearing and pressing device comprises a spring unit, the spring unit comprises one or more plate spring elements, the one or more plate spring elements comprises an annular shaped form; and
in which the one or more plate spring element comprises one or more circular-ring-shaped plate spring element, an outer edge of the circular-ring-shaped plate spring element being connected via at least one first wall to a substantially rigid annular support part, an inner edge of the circular-ring-shaped plate spring element being connected via at least one second wall to a substantially rigid base part, the substantially rigid base part being coupled to the rotor to transmit a pressing force to the rotor.

17. The switching valve of claim 16 further comprising: a coupling element to connect the rotor and the substantially rigid base part.

18. The switching valve of claim 16, in which
(a) the first and second walls have a rigidity under extension in a longitudinal direction where a spring travel of the plate spring element is defined substantially by the spring travel, and
(b) the first and second walls have a rigidity under bending under compression movements of a plate spring region of the plate spring element are permitted by elastic bending deformation of the first and second walls.

19. The switching valve of claim 18, in which the first and second walls are configured to generate restoring forces and restoring moments so that a spring characteristic of the plate spring region remains substantially unchanged when subjected to bending deformations.

20. The switching valve of claim 19, in which the first wall and the second wall are in each case of an encircling form and configured to rigidly hold the plate spring region and the base part with respect to translatory movements in a plane perpendicular to the axis of the plate spring region to secure a radial positioning of the rotor relative to the stator.

21. The switching valve of claim 17, in which the base part includes one or more pin-shaped coupling elements to radially position the rotor and to rotationally conjointly connect to the rotor.

* * * * *